United States Patent
Skubsch et al.

(10) Patent No.: US 10,568,817 B2
(45) Date of Patent: Feb. 25, 2020

(54) COSMETIC SPRAY

(71) Applicant: BEIERSDORF AG, Hamburg (DE)

(72) Inventors: Kerstin Skubsch, Prisdorf (DE); Kaja Luettig, Hamburg (DE); Claudia Mueller, Tangstedt (DE); Regine Werner, Bienenbuettel (DE); Anke Huelshoff, Tangstedt (DE)

(73) Assignee: BEIERSDORF AG, Hamburg (DE)

( * ) Notice: Subject to any disclaimer, the term of this patent is extended or adjusted under 35 U.S.C. 154(b) by 0 days.

(21) Appl. No.: 15/516,701

(22) PCT Filed: Sep. 25, 2015

(86) PCT No.: PCT/EP2015/072079
§ 371 (c)(1),
(2) Date: Apr. 4, 2017

(87) PCT Pub. No.: WO2016/055287
PCT Pub. Date: Apr. 14, 2016

(65) Prior Publication Data
US 2017/0296445 A1 Oct. 19, 2017

(30) Foreign Application Priority Data
Oct. 9, 2014 (DE) .................. 10 2014 220 449

(51) Int. Cl.
*A61K 8/04* (2006.01)
*A61K 8/06* (2006.01)
*A61K 8/37* (2006.01)
*B65D 83/62* (2006.01)
*A61K 8/39* (2006.01)
*B65D 83/14* (2006.01)
*A61K 8/81* (2006.01)
*A61Q 19/00* (2006.01)

(52) U.S. Cl.
CPC ............. *A61K 8/062* (2013.01); *A61K 8/046* (2013.01); *A61K 8/375* (2013.01); *A61K 8/39* (2013.01); *A61K 8/8152* (2013.01); *A61Q 19/00* (2013.01); *A61Q 19/007* (2013.01); *B65D 83/62* (2013.01); *B65D 83/752* (2013.01); *A61K 2800/87* (2013.01)

(58) Field of Classification Search
CPC ................................ A61K 8/062; B65D 83/62
See application file for complete search history.

(56) References Cited

U.S. PATENT DOCUMENTS

| | | | | |
|---|---|---|---|---|
| 9,211,995 | B2 * | 12/2015 | Werner | B65D 33/00 |
| 2003/0017176 | A1 * | 1/2003 | Bleckmann | A61K 8/06 |
| | | | | 424/401 |
| 2003/0235539 | A1 * | 12/2003 | Mongiat | A61K 8/4913 |
| | | | | 424/59 |
| 2005/0124705 | A1 | 6/2005 | Schreiber et al. | |
| 2013/0142746 | A1 * | 6/2013 | Demson | A61K 8/345 |
| | | | | 424/70.1 |
| 2013/0233310 | A1 | 9/2013 | Hilgers et al. | |
| 2013/0345647 | A1 * | 12/2013 | Har-Shai | A62C 13/00 |
| | | | | 604/257 |
| 2014/0140940 | A1 | 5/2014 | Von Thaden et al. | |

FOREIGN PATENT DOCUMENTS

| | | |
|---|---|---|
| DE | 102011077017 A1 | 12/2012 |
| DE | 102011077018 A1 | 12/2012 |
| DE | 102011077028 A1 | 12/2012 |
| DE | 102011077031 A1 | 12/2012 |
| DE | 102011077037 A1 | 12/2012 |
| DE | 102011077060 A1 | 12/2012 |
| EP | 2636401 A1 | 9/2013 |
| FR | 2924020 A1 | 5/2009 |
| FR | 2929845 A1 | 10/2009 |
| WO | 2012167905 A2 | 12/2012 |

OTHER PUBLICATIONS

Anonymous: "GNPD—Intensive Serum", Aug. 1, 2014 (Aug. 1, 2014) Retrieved from Internet on Oct. 21, 2014: URL:http://www.gnpd.com/sinatra/recordpage/2609761/from search//CDXUQvfu9/.
Anonymous: "GNPD—Emulsion"; Jul. 1, 2014 (Jul. 1, 2014) Retrieved from Internet on Oct. 21, 2015: URL:http://www.gnpd.com/sinatra/recordpage/2556917/from search//CDXUQvIu9/.
Anonymous: "Technology: BoV : Bag on Valve system : Aerosols filling : Pump Spray : Bag on Valve" Sep. 9, 2013 (Sep. 9, 2013), Retrieved from Internet on Oct. 19, 2015: URL:https://web.archive.org/web/20130909013727/http://www.bagonvalve.com/technology/.
Anonymous: "GNPD—48H Anti-Frizz Milky Serum", Sep. 1, 2014 (Sep. 1, 2014) Retrieved from Internet on Oct. 21, 2015: URL:http://www.gnpd.com/sinatra/recordpage/2661649/from search//CDXUQvfu9/.

\* cited by examiner

*Primary Examiner* — Kyle A Purdy
(74) *Attorney, Agent, or Firm* — Abel Schillinger, LLP

(57) ABSTRACT

The invention relates to a cosmetic spray consisting of a) an oil-in-water emulsion (O/W emulsion) containing poly glyceryl-10 stearate and b) a spray applicator system.

20 Claims, No Drawings

COSMETIC SPRAY

BACKGROUND OF THE INVENTION

1. Field of the Invention

The present invention relates to a cosmetic spray consisting of an oil-in-water emulsion (O/W emulsion) containing polyglyceryl-10 stearate and also a spray applicator system.

2. Discussion of Background Information

The desire to appear beautiful and attractive is naturally rooted in humans. Even if the beauty ideal has changed over the course of time, striving after a flawless appearance has always been the aim of humans. An essential part of a beautiful and attractive appearance is the condition and appearance of the skin.

Skincare products generally consist of emulsions. Emulsions are generally understood to mean heterogeneous systems which consist of two liquids immiscible, or of only limited miscibility, with each other, which are typically referred to as phases and in which one of the two liquids is dispersed in the form of fine droplets in the other liquid. Externally and with the naked eye, emulsions appear homogeneous.

If the two liquids are water and oil and oil droplets are present finely divided in water, it is an oil-in-water emulsion (O/W emulsion, e.g. milk). The basic character of an O/W emulsion is characterized by the water. In a water-in-oil emulsion (W/O emulsion, e.g. butter), the principle is reversed and the basic character is determined here by the oil.

The abundance of commercially available cosmetic emulsions should not however obscure the fact that these preparations of the prior art have a series of disadvantages.

Particularly when these emulsions are applied directly on to the skin using a spray applicator system, e.g. an aerosol can or a bag-on-valve system (see below) from a reservoir under pressure, the problem arises that the preparations on the one hand should be stable to temperature and on storage and not prone to premature phase separation and on the other hand must be sufficiently thin to be sprayable at all.

Furthermore, in these preparations which are released by positive pressure, the problem always arises that the pressure decreases with increasing application time or on repeated application of the pressure with which the preparation is conveyed out from the reservoir, such that with decreasing pressure the preparation is "shot" (conveyed out) by the dispenser in the spray head. In the preparations from the prior art, this results in a markedly modified spray pattern of the atomized preparation over the course of the service life of the product. The droplet dispersion of the atomized preparation changes progressively the larger the size of the sprayed area (at constant distance), the spray pattern becomes much more non-uniform and an increasing number of droplets achieve acceleration that is too low and therefore fall to the ground before reaching a target located at a horizontal distance.

SUMMARY OF THE INVENTION

It was therefore the object of the present invention to eliminate the deficiencies of the prior art and to develop a cosmetic spray whose spray pattern remains as constant as possible over different spray pressure stages.

The object, surprisingly, is achieved by a cosmetic spray consisting of
a) an oil-in-water emulsion (O/W emulsion) containing polyglyceryl-10 stearate and also
b) a spray applicator system.

Although the prior art knows DE 102011077017, DE 102011077018, DE 102011077028, DE 102011077031, DE 102011077060, nevertheless these documents were not able to direct the way to the present invention.

It is preferred according to the invention in this case if the spray applicator system used is a bag-on-valve applicator system, in which a bag containing the O/W emulsion is in a pressurized gas container under positive pressure.

In the case of these bag-on-valve systems, the contents of the bag (in this case the O/W emulsion) is pressed outwards by the spray head by the positive pressure in the pressurized gas container on opening the spray head and divided into small droplets ("spray mist") by the dispenser present in the spray head. The pressure compensation therefore does not occur by the direct escape of the pressurized gas from the positive pressure container, but through emptying the contents of the storage bag.

It is advantageous according to the invention if the positive pressure in the pressurized gas container of the bag-on-valve applicator system is from 2 to 12 bar (based on the ambient pressure of 1.013 bar).

It is advantageous in accordance with the invention if the spray head of the spray applicator has a uniform spray jet over the entire lifetime of the can. From a distance of 10 cm, a spray pattern of 5-6 cm is favored. If the pressure falls over the entire lifetime of the can, the spray pattern should not exceed 8 cm.

According to the invention, advantageous embodiments of the present invention are characterized in that the bag containing the O/W emulsion is formed from a laminate of PE/adhesive/PA/adhesive/AL/adhesive/PET.

Particularly preferred according to the invention is a spray applicator with the following specification: filling 8 bar positive pressure with nitrogen valve DU 3527 or DU 2537 from Aptar®, BOV—cup: Alu gold lacquered—inner gasket: Buna KA 6712—body valve: PP—spring: Inox c302—piston: POM—external gasket: butyl 1.2 mm foil: PET12/ALU8/OPA15/PP75.

In the context of the present invention, it is advantageous if the O/W emulsion according to the invention contains from 0.1 to 2% by weight of polyglyceryl-10 stearate, based on the total weight of the emulsion.

In the context of the present invention, it is preferred if the O/W emulsion according to the invention contains from 0.5 to 1.0% by weight of polyglyceryl-10 stearate, based on the total weight of the emulsion.

According to the invention, advantageous embodiments of the present invention are characterized in that the emulsion comprises acrylate/C10-30 alkyl acrylate crosspolymer.

In such a case, according to the invention, it is advantageous if the emulsion contains from 0.02 to 0.2% by weight of acrylate/C10-30 alkyl acrylate crosspolymer, based on the total weight of the emulsion. According to the invention, the concentration range of from 0.05 to 0.15% by weight, based on the total weight of the emulsion is preferred here.

It is advantageous in accordance with the invention if the emulsion contains caprylic/capric triglyceride, isopropyl palmitate and/or shea butter.

If the emulsion contains caprylic/capric triglyceride, it is advantageous in accordance with the invention if this substance is present in this at a concentration of 1 to 7% by weight, based on the total weight of the emulsion.

If the emulsion contains isopropyl palmitate, it is advantageous in accordance with the invention if this substance is present in this at a concentration of 1 to 7% by weight, based on the total weight of the emulsion.

If the emulsion contains shea butter, it is advantageous in accordance with the invention if this substance is present in this at a concentration of 0.5 to 3% by weight, based on the total weight of the emulsion.

According to the invention, advantageous embodiments of the present invention are also characterized in that the emulsion contains dimethicone and/or cyclomethicone.

The oil phase of the emulsion according to the invention may also contain further oil, fat and wax components, for example, polar oils from the group of the lecithins or compounds such as cocoglyceride, olive oil, sunflower oil, jojoba oil, soybean oil, peanut oil, rapeseed oil, almond oil, palm oil, coconut oil, castor oil, wheat germ oil, grape seed oil, safflower oil, evening primrose oil, macadamia nut oil and the like. It is also possible to use compounds such as phenethyl benzoate, 2-phenylethyl benzoate, isopropyl lauroyl sarcosinate, phenyl trimethicone, cyclomethicone, dibutyl adipate, octyl palmitate, octyl cocoate, octyl isostearate, octyldodecyl myristate, octyldodecanol, cetearyl isononanoate, isopropyl myristate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, stearyl heptanoate, oleyl oleate, oleyl erucate, erucyl oleate, erucyl erucate, tridecyl stearate, tridecyl trimellitate.

Also advantageous in accordance with the invention are, for example, natural waxes of animal and vegetable origin such as beeswax and other insect waxes and berry wax, shea butter and/or lanolin (wool wax).

The oil phase may also be selected advantageously from the group of dialkyl ethers and dialkyl carbonates, e.g. dicaprylyl ether (Cetiol OE) and/or dicaprylyl carbonate, which may be obtained from Cognis for example under the trade name Cetiol CC, are advantageous.

It is also advantageous to select the oil component(s) from the group isoeicosan, neopentyl glycol diheptanoate, propylene glycol dicaprylate/dicaprate, caprylic/capric/diglyceryl succinate, butylene glycol dicaprylate/dicaprate, $C_{12-13}$-alkyl lactate, di-$C_{12-13}$-alkyl tartrate, triisostearin, dipentaerythrityl hexacaprylate/hexacaprate, propylene glycol monoisostearate, tricaprylin, dimethyl isosorbide. It is in particular advantageous if the oil phase of the formulations according to the invention has a $C_{12-15}$-alkyl benzoate content.

Any mixtures of such oil and wax components can also be used advantageously in the context of the present invention.

The oil phase can likewise also further comprise advantageously non-polar oils, for example those which are selected from the group of branched and straight-chain hydrocarbons and waxes, especially mineral oil, vaseline (petrolatum), paraffin oil, squalane and squalene, polyolefins, hydrogenated polyisobutenes, C13-16 isoparaffin and isohexadecane. In terms of polyolefins, the preferred substances are polydecenes.

It is advantageous in accordance with the invention if the emulsion according to the invention contains ethanol and/or glycerol.

If the emulsion contains ethanol, a use concentration of 0.5 to 8% by weight, based on the total weight of the emulsion, is advantageous in accordance with the invention.

If the emulsion contains glycerol, a use concentration of 1 to 12% by weight, based on the total weight of the emulsion, is advantageous in accordance with the invention.

Advantageous embodiments of the present invention are also characterized in that the emulsion comprises one or more active ingredients selected from the group of compounds UV filters, magnolia extract, glycyrrhetic acid, urea, arctiin, alpha-lipoic acid, folic acid, phytoene, D-biotin, coenzyme Q10, alpha-glucosyls tin, carnitine, carnosine, caffeine, natural and/or synthetic isoflavonoids, glycerylglucose, creatine, creatinine, taurine, tocopherol, tocopherol acetate, β-alanine and/or licochalcone A.

In accordance with the invention, advantageous UV filters may be selected, for example, from the group of the compounds 2-phenylbenzimidazole-5-sulfonic acid and/or salts thereof; phenylene-1,4-bis(2-benzimidazyl)-3,3'-5,5'-tetrasulfonic acid salts; 1,4-di(2-oxo-10-sulfo-3-bornylidenemethyl)benzene and salts thereof; 4-(2-oxo-3-bornylidenemethyl)benzenesulfonic acid salts; 2-methyl-5-(2-oxo-3-bornylidenemethypsulfonic acid salts; 2,2'-methylenebis(6-(2H-benzotriazol-2-yl)-4-(1,1,3,3-tetramethylbutyl)phenol); 2-(2H-benzotriazol-2-yl)-4-methyl-6-[2-methyl-3-[1,3,3,3-tetramethyl-1-[(trimethylsilyl)oxy]disiloxanyl]propyl]phenol; 3-(4-methylbenzylidene)camphor; 3-benzylidenecamphor; ethylhexyl salicylate; terephthalidenedicamphorsulfonic acid; 2-ethylhexyl 2-cyano-3,3-diphenylacrylate; 2-ethylhexyl 4-(dimethylamino)benzoate; amyl 4-(dimethylamino)benzoate; di(2-ethylhexyl) 4-methoxybenzalmalonate; 2-ethylhexyl 4-methoxycinnamate; isoamyl 4-methoxycinnamate; 2-hydroxy-4-methoxybenzophenone, 2-hydroxy-4-methoxy-4'-methylbenzophenone; 2,2'-dihydroxy-4-methoxybenzophenone; homomenthyl salicylate; 2-ethylhexyl 2-hydroxybenzoate; dimethicodiethylbenzalmalonate; 3-(4-(2,2-bis ethoxycarbonylvinyl)phenoxy)propenyl)methoxysiloxane/dimethylsiloxane-copolymer; 4-(tert-butyl)-4'-methoxydibenzoylmethane; hexyl 2-(4'-diethylamino-2'-hydoxybenzoyl)benzoate; dioctylbutylamidotriazone (INCI: Diethylhexyl Butamidotriazone); 2,4-bis[5-1(dimethylpropyl)benzoxazol-2-yl-(4-phenyl)imino]-6-(2-ethexyl)imino-1,3,5-triazine with (CAS No. 288254-16-0); 2,4-bis {[4-(2-ethylhexyloxy)-2-hydroxy]phenyl}-6-(4-methoxyphenyl)-1,3,5-triazine (INCI Bis-Ethylhexyloxyphenol Methoxyphenyl Triazine); tris(2-ethylhexyl) 4,4',4"-(1,3,5-triazine-2,4,6-triyltriimino)trisbenzoate (also: 2,4,6-tris[anilitio-(p-carbo-2'-ethyl-1'-hexyloxy)]-1,3,5-triazine (INCI: Ethylhexyl Triazone); 2,4,6-tribiphenyl-4-yl-1,3,5-triazine; merocyanine; titanium dioxide; zinc oxide.

It is advantageous according to the invention if the emulsion contains ethylhexylglycerin, propylene glycol, butylene glycol, 2-methylpropane-1,3-diol, 1,2-pentanediol, 1,2-hexanediol, 1,2-octanediol, piroctone olamine and/or 1,2-decanediol.

In accordance with the invention, advantageous embodiments of the present invention are characterized in that the emulsion contains phenoxyethanol and/or methylparaben. It is advantageous in accordance with the invention if the emulsion is free of propylparaben and butylparaben.

In accordance with the invention, advantageous embodiments are also characterized in that the emulsion contains at least 70% by weight water, based on the total weight of the emulsion.

Comparative Test

With the following test, the effect according to the invention could be exemplified:

|  | Sample A | Sample B |
| --- | --- | --- |
| Polyglyceryl-10 Stearate | 0.7 |  |
| Polyglyceryl-3 Methyglucose Distearate |  | 0.7 |
| Acrylates/C10-30 alkyl acrylate crosspolymer | 0.1 | 0.1 |
| Caprylic/Capric Triglyceride | 5 | 5 |
| Isopropyl Palmitate | 5 | 5 |
| *Butyrospermum Parkii* Butter | 1 | 1 |
| Dimethicone | 1 | 1 |
| Glycerol | 7 | 7 |

-continued

|  | Sample A | Sample B |
|---|---|---|
| 45% aqueous sodium hydroxide solution | 0.07 | 0.07 |
| Phenoxyethanol | 0.8 | 0.8 |
| Methylparaben | 0.3 | 0.3 |
| Aqua | 76.03 | 76.03 |
| Alcohol | 3 | 3 |

Filling 8 bar positive pressure with nitrogen
valve DU 3527 from Aptar®
BOV—cup: Alu gold lacquered—inner gasket: Buna KA 6712—body valve: PP—spring: Inox c302—piston: POM—external gasket: butyl 1.2 mm foil: PET12/ALU8/OPA15/PP75.

The samples were sprayed vertically onto blue paper from a distance of 10 cm. Sample A shows a relatively uniform circular spray pattern of ca. 5-10 cm diameter over the whole application period and reducing pressure in the can linked thereto (from 8 bar down to 3 bar). Conversely, sample B changes its spray pattern very significantly with decreasing pressure. At full can filling of ca. 8 bar, said sample shows a round circle of ca. 8 cm diameter. With decreasing amount/pressure, the spray pattern develops an elongated double jet pattern of ca. 20 cm width. Therefore, the product cannot be applied uniformly.

DETAILED DESCRIPTION OF EMBODIMENTS OF THE INVENTION

Examples

The following examples are intended to clarify the present invention without limiting it. All quantitative data, fractions and percentages, unless otherwise stated, are specified based on the weight and the total amount or on the total weight of the preparations respectively.

|  | A % | B % | C % | D % |
|---|---|---|---|---|
| Polyglyceryl-10 Stearate | 0.7 | 0.5 | 0.7 | 0.6 |
| Acrylates/C10-30 alkyl acrylate crosspolymer | 0.12 | 0.1 | 0.1 | 0.1 |
| Xanthan Gum |  | 0.05 |  | 0.1 |
| Caprylic/Capric Triglyceride | 5 | 4 | 4 | 2 |
| Isopropyl Palmitate | 5 |  | 6 | 3 |
| *Butyrospermum Parkii* Butter | 1 |  | 0.5 | 1 |
| Dimethicone | 0.9 |  | 1 |  |
| C12-15 Alkyl benzoate |  |  |  | 3 |
| Almond oil | 2 |  |  |  |
| Dicaprylyl Ether |  | 5 |  |  |
| Glycerol | 7 | 9 | 8 | 5 |
| Phenoxyethanol | 0.8 | 0.5 | 0.5 | 0.5 |
| Methylparaben | 0.3 | 0.2 | 0.3 | 0.3 |
| Cocoa butter |  | 1 |  |  |
| Tocopherol acetate |  | 0.5 |  |  |
| Alcohol | 3 | 1 | 2 | 3 |
| Perfume | 0.3 | 0.35 | 0.3 |  |
| Aqueous sodium hydroxide solution | pH adjustment | pH adjustment | pH adjustment | pH adjustment |
| Water | to 100 | to 100 | to 100 | to 100 |
| Initial pressure in bar | 8 | 9 | 7 | 8 |
| Pressurized gas | nitrogen | nitrogen | nitrogen | nitrogen |
| Spray valve | DU 3527 | DU 3520 | DU 3527 | DU 3527 |

BOV applicator system, e.g. from Aptar®
Ex-EP BOV cup: Mu gold lacquered—inner gasket: Buna KA 6712—body valve: PP—spring: Inox 302—piston: POM—external gasket: butyl 1.2 mm foil: PET12/ALU8/OPA15/PP75

What is claimed is:

1. A cosmetic spray product, wherein the spray product consists of
   (a) an oil-in-water emulsion (O/W emulsion) comprising polyglyceryl-10 stearate; and
   (b) a spray applicator system which is a bag-on-valve applicator system in which a bag containing the O/W emulsion is present in a pressurized gas container under positive pressure, the system featuring: filling 8 bar positive pressure with nitrogen valve BOV—cup: Alu gold lacquered—inner gasket: Buna KA 6712—body valve: PP—spring: Inox c302—piston: POM—external gasket: butyl 1.2 mm foil: PET 12/ALU8/OPA15/PP75.

2. The cosmetic spray product of claim 1, wherein the O/W emulsion comprises from 0.1% to 2% by weight of polyglyceryl-10 stearate, based on a total weight of the emulsion.

3. The cosmetic spray product of claim 2, wherein the emulsion further comprises from 0.02% to 0.2% by weight of acrylate/C10-30 alkyl acrylate crosspolymer, based on a total weight of the emulsion.

4. The cosmetic spray product of claim 2, wherein the emulsion further comprises caprylic/capric triglyceride, isopropyl palmitate, and shea butter.

5. The cosmetic spray product of claim 2, wherein the emulsion further comprises dimethicone and/or cyclomethicone.

6. The cosmetic spray product of claim 1, wherein the emulsion comprises at least 70% by weight of water, based on a total weight of the emulsion.

7. A cosmetic spray product, wherein the spray product consists of
(a) an oil-in-water emulsion (O/W emulsion) comprising from 0.1% to 2% by weight of polyglyceryl-10 stearate, based on a total weight of the emulsion; and
(b) a spray applicator system;
and wherein a spray head of the spray applicator system provides a uniform spray jet over an entire lifetime of the cosmetic spray product.

8. The cosmetic spray of claim 7, wherein the spray applicator system provides a spray pattern of about 5-10 cm diameter when the emulsion is sprayed vertically from a distance of 10 cm at a pressure of from 8 bar down to 3 bar.

9. The cosmetic spray of claim 8, wherein the spray applicator system provides a spray pattern of about 5-6 cm diameter.

10. The cosmetic spray of claim 7, wherein the spray applicator system is a bag-on-valve applicator system, in which a bag containing the O/W emulsion is present in a pressurized gas container under positive pressure.

11. The cosmetic spray product of claim 10, wherein the spray applicator system is a system featuring: filling 8 bar positive pressure with nitrogen valve DU 3527 or DU 2537 from Aptar®, BOV—cup: Alu gold lacquered—inner gasket: Buna KA 6712—body valve: PP—spring: Inox c302—piston: POM—external gasket: butyl 1.2 mm foil: PET12/ALU8/OPA15/PP75.

12. The cosmetic spray of claim 7, wherein the emulsion further comprises shea butter.

13. The cosmetic spray product of claim 7, wherein the emulsion further comprises dimethicone and/or cyclomethicone.

14. A cosmetic spray product, wherein the spray product consists of
(a) an oil-in-water emulsion (O/W emulsion) comprising from 0.5% to 1.0% by weight of polyglyceryl-10 stearate, from 0.05% to 0.15% by weight of acrylate/C10-30 alkyl acrylate crosspolymer, from 1% to 7% by weight of caprylic/capric triglyceride, from 1% to 7% by weight of isopropyl palmitate, and from 0.5% to 3% by weight of shea butter, based on a total weight of the emulsion; and
(b) a spray applicator system.

15. The cosmetic spray product of claim 14, wherein the emulsion further comprises dimethicone and/or cyclomethicone.

16. The cosmetic spray product of claim 14, wherein the emulsion comprises from 5% to 7% by weight of caprylic/capric triglyceride and from 5% to 7% by weight of isopropyl palmitate.

17. The cosmetic spray product of claim 14, wherein the emulsion comprises at least 70% by weight of water, based on a total weight of the emulsion.

18. The cosmetic spray product of claim 14, wherein a spray head of the spray applicator system provides a uniform spray jet over an entire lifetime of the cosmetic spray.

19. The cosmetic spray product of claim 14, wherein the spray applicator system provides a spray pattern of about 5-10 cm diameter when the emulsion is sprayed vertically from a distance of 10 cm at a pressure of from 8 bar down to 3 bar.

20. The cosmetic spray product of claim 14, wherein the spray applicator system is a bag-on-valve applicator system in which a bag containing the O/W emulsion is present in a pressurized gas container under positive pressure, the system featuring: filling 8 bar positive pressure with nitrogen valve DU 3527 or DU 2537 from Aptar®, BOV—cup: Alu gold lacquered—inner gasket: Buna KA 6712—body valve: PP—spring: Inox c302—piston: POM—external gasket: butyl 1.2 mm foil: PET12/ALU8/OPA15/PP75.

* * * * *